United States Patent [19]
Custer et al.

[11] 4,143,655
[45] Mar. 13, 1979

[54] METHOD AND APPARATUS FOR APPLYING HEAT SOFTENABLE ORTHOPEDIC CAST

[75] Inventors: Milton F. Custer, Livermore; Carol J. Laufenberg, Pleasanton, both of Calif.

[73] Assignee: Hexcel Corporation, San Francisco, Calif.

[21] Appl. No.: 826,437

[22] Filed: Aug. 22, 1977

[51] Int. Cl.² .................................................. A61F 5/04
[52] U.S. Cl. ..................................... 128/90; 128/156
[58] Field of Search ............... 128/155, 156, 90, 89 R; 264/222

[56] References Cited
U.S. PATENT DOCUMENTS

| 3,692,023 | 9/1972 | Phillips et al. | 128/90 |
| 4,019,505 | 4/1977 | Wartman | 128/90 |

*Primary Examiner*—John D. Yasko
*Attorney, Agent, or Firm*—Townsend and Townsend

[57] ABSTRACT

A heat softenable orthopedic bandage assembly which comprises a length of a pliant fabric material to which a heat softenable polymer composition is applied. The fabric material is wound up into a roll and a separator is placed between adjacent fabric convolutions of the roll. The separator is constructed of a material that is readily releasable from the heat softenable composition, it is relatively thin, and includes a multiplicity of apertures which have a size less than the size of the openings in the fabric carrier. The cast is formed by submerging the roll in heated water to heat the temperature of the composition above its softening temperature. While submerged water is flowed in a radial direction past the carrier openings and the separator apertures towards the center of the roll to speed up the softening process. When the roll is removed from the water to form the orthopedic cast the separator prolongs the cool-down time over what it would be if no separator were used to extend the available time during which the cast may be formed.

31 Claims, 5 Drawing Figures

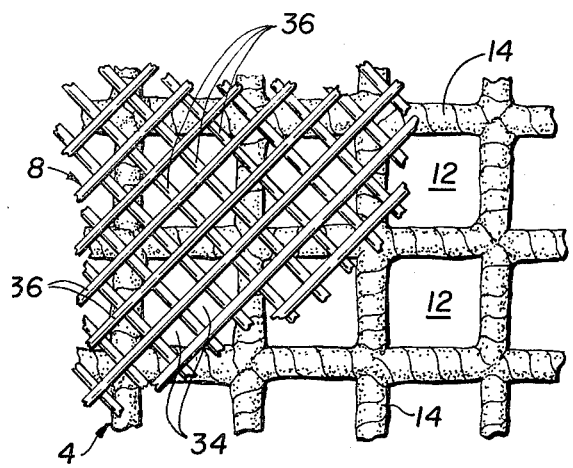
FIG._1.
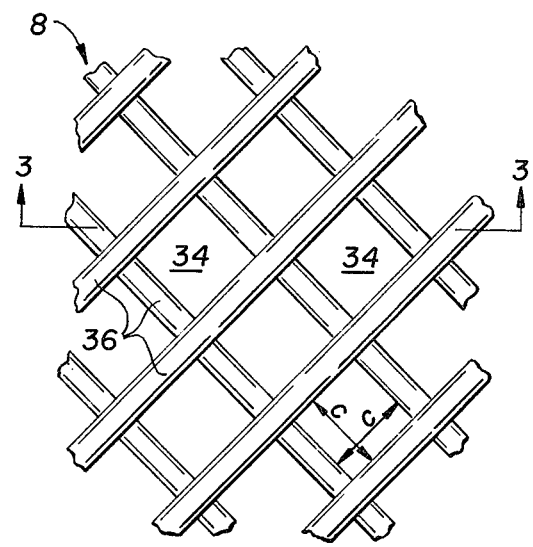
FIG._2.
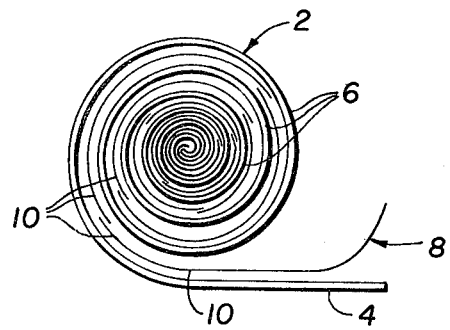
FIG._4.
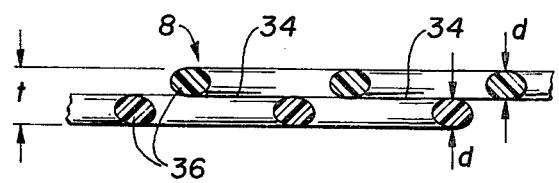
FIG._3.
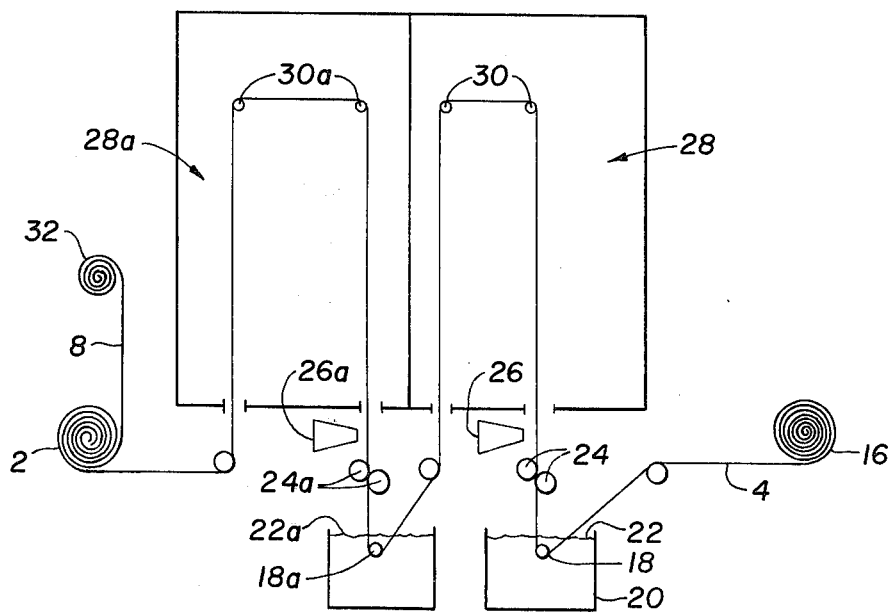
FIG._5.

METHOD AND APPARATUS FOR APPLYING HEAT SOFTENABLE ORTHOPEDIC CAST

BACKGROUND OF THE INVENTION

In the recent past, orthopedic casts formed from materials other than the theretofor conventional plaster of paris have found increasing acceptance. Usually, such orthopedic casts employ a carrier or bandage coated with a material that can be temporarily softened while the bandage is wrapped about the affected body portion, say a limb, and which thereafter hardens. Alternatively, such bandages may be used in conjunction with materials that are hardened by applying physical agents (such as ultraviolet radiation, ultrasound or heat) or chemical reactants to them.

One particularly successful orthopedic bandage, marketed by the assignee of this application under its trademark HEXCELITE, utilizes a carrier having relatively large openings (defined by a fabric of widely spaced apart strands) to which a heat softenable polymer composition is applied. A length, say six feet or more of the bandage is wound into a roll and the roll is immersed in heated water. After the entirety of the roll has reached the desired temperature so that all of the polymer composition is heat softened, the roll is removed from the water and the bandage is unwound about the person's limb to form the orthopedic cast. When the temperature of the compound with which the carrier is impregnated falls below its softening temperature the cast rigidifies.

The resulting cast exhibits excellent strength, abrasion and impact resistance. Yet it is much lighter than conventional plaster casts and other prior art casts. Further, the large openings defined by the carrier permit good air access to the underlying skin to prevent skin maceration.

In addition to having the proper wearing characteristics, materials from which orthopedic casts are made must, of course, lead themselves to being formed into a cast. This requires that the material must be quickly available for forming it into the cast and that it harden promptly while leaving sufficient time so that it can be formed or molded into the cast. Additionally, the material must not cause discomfort or injury due to such factors as excessive heat, poisonous or noxious substances and the like.

Heat softenable orthopedic bandages such as the one marketed under the trademark HEXCELITE percent a twofold problem. First, the bandage roll convolutions must be prevented from adhering to each other when the polymer composition is heat softened or the bandage cannot be conveniently applied. Secondly, the bandage and in particular the polymer composition should heat up quickly when placed in a heating medium, typically a heated water bath. Once the heated bandage is removed from the bath, however, it should remain in its softened state for a sufficient length of time, preferably for six or seven to 10 minutes, to enable the molding of the cast before the polymer composition cools to below its softening temperature and hardens. The desired quick heating and slow cooling of the bandage, however, are not entirely compatible because one normally precludes the other. For example, in the case of HEXCELITE bandages, which typically have bandage openings of around 0.025 in$^2$, the immersion of a 2-$\frac{3}{4}$ in. roll in water of 165° F. requires only about $\frac{1}{2}$ minute to heat it up. However, the roll, once removed from the bath, cools to below the softening temperature of the polymer composition in as little as five to 5$\frac{1}{2}$ minutes, often an insufficient time period for forming a cast.

To overcome both the problem of bonded bandage convolutions and a short cool down period orthopedic bandages such as the one marketed under the trademark HEXCELITE, as well as others, employ "release films" that are placed between the convolutions of the bandage roll. These release films prevent an adherence of adjacent bandage convolutions when the roll is heated and further slow down the cooling rate of the roll once removed from the heated water bath so as to give the person forming the cast sufficient time to fully apply the bandage. A drawback of such release films is the fact that they significantly prolong the time required for fully heating the bandage roll because they greatly inhibit water circulation through the roll. However, since the bandage often cannot be effectively applied unless the bandage roll remains in its heat softened, pliable state for substantially more than five minutes, say seven to 10 minutes, the drawback of prolonged water submersion times was accepted as the lesser of two evils, particularly since the release film significantly reduced the heat loss and, under the conditions of the above example, typically prolonged the available time to form the heated bandage into the orthopedic cast to well in excess of 10 minutes.

Prior art patents which demonstrate the present state-of-the-art in regard to bandage material for forming orthopedic casts as discussed above include the following U.S. Pat. Nos.: 3,420,231; 3,763,858; 3,935,355.

SUMMARY OF THE INVENTION

The present invention is generally applicable to orthopedic bandages of the type in which a bandage roll must be heated to render it soft and pliable for molding the bandage into an orthopedic cast and it is particularly advantageously used in connection with the above-identified HEXCELITE orthopedic bandage. Broadly speaking, the present invention replaces the heretofore used release films between adjacent convolutions of a bandage roll with a perforated separator which has a multiplicity of evenly distributed, closely adjacent apertures each of which has a size substantially less than the size of the openings in the bandage. The separator normally has a width and a length compatible with that of the bandage and it is further relatively thin to prevent an undue increase in the diameter of a six foot bandage roll (which is generally considered the minimum length for an orthopedic bandage) which would render it difficult or inconvenient to handle.

The provision of such a separator prevents the earlier discussed adherence of adjacent bandage convolutions when the polymer composition is heated above its softening point. This holds true even though the separator is relatively thin, its thickness usually being in the order of no more than about a few hundredths of an inch. Although the exact reason why there is no or no significant amount of bonding between the heat softened polymer compositions of adjoining bandage convolutions it is believed that the small hole size and the relatively high surface tension of heat softened polymer compositions prevent a substantial penetration of the separator apertures by the composition. In addition, whatever polymer penetration may occur is limited to the relatively small aperture size and is frequently interrupted by the cross strands of the separator so that there is no single large bonded surface area between adjoining convolutions. This greatly facilitates the release of such bonds, if in fact they occur, as the bandage is unrolled.

Aside from its excellent ability to effectively prevent a cross bonding between adjoining bandage convolutions in the heated roll, the separator of the present invention further significantly speeds up the heating of the roll once immersed in the heated medium, usually a heated water bath because it permits the water to flow in a radial direction towards the center of the roll in addition to whatever axial water flow between the bandage convolutions takes place. As a consequence, the heat up time for the above-discussed six foot long bandage roll discussed in the earlier example, when placed in a 165° F. water bath is reduced from approximately eight minutes (when a "release film" is wound up with the bandage) to approximately half a minute, i.e., about the same heat up time as is experienced when the bandage is wound up without any release film or separate between its convolutions. The heat up time is thereby reduced to the desired short time interval.

Although one would expect that the incorporation of the perforated separator of the present invention would reduce the cool down period in roughly the same proportion as the heat up period is reduced, applicants quite surprisingly discovered that the use of such a separator significantly increases the cool down period over what it would be if no separator were used. In the discussed example, the average cool down period for a six foot long bandage roll provided with a separator is approximately 9-½ minutes, close to twice the cool down period for a six foot bandage roll without a release film or a separator even though the heat up periods are substantially identical. Applicants have not determined the exact reason why this discrepancy in the heat up and cool down periods occurs since logic would seem to dictate that a reduction in one should entail a similar reduction in the other and vice versa. It is speculated, however, that at least one of the reasons for such a differential change in the cool down and heat up periods is the fact that the much denser heated water quickly and relatively freely penetrates to the center of the bandage roll. Upon the removal of the roll from the water bath, however, cooling air penetrates to the center much more slowly, in fact it appears that the many small apertures of the separator substantially inhibit ambient air from flowing towards the center of the roll. Further, significant amounts of heated water are retained in the small apertures. This water acts as a heat sink and further inhibits the entrance of cooling air to the center of the roll so that the center of the roll stays heated for a much longer time period than a bandage roll having no separator.

BRIEF DESCRIPTION OF THE DRAWINGS

FIG. 1 is a fragmentary plan view showing a separator constructed in accordance with the present invention superimposed over an orthopedic bandage material treated with a heat softenable polymer composition;

FIG. 2 is an enlarged, fragmentary plan view of the separator illustrated in FIG. 1;

FIG. 3 is a side elevational view, in section, and is taken on line 3-3 of FIG. 2;

FIG. 4 is a plan view of an orthopedic bandage roll in which a separator constructed in accordance with the present invention is rolled up together with the bandage to separate adjoining bandage convolutions; and FIG. 5 is a diagrammatic view showing a method of fabricating a resin impregnated bandage and winding the bandage together with a separator constructed in accordance with the present invention into a bandage roll.

DESCRIPTION OF THE PREFERRED EMBODIMENTS

Referring first briefly to FIG. 4, an orthopedic bandage roll 2 constructed in accordance with the present invention generally comprises an elongate, flexible, rolled up carrier or bandage 4, normally of a length of at least about six feet, which defines a multitude of bandage convolutions 6. Wound up with the bandage is in elongate, perforated separator 8 which is constructed as is more fully described below and which may be defined by a single, continuous separator or by a plurality of serially arranged separator sections 10 which have a combined or effective length substantially equal to that of the bandage. A heat softenable material is applied to the bandage which renders the bandage substantially rigid at normal temperatures, preferably at temperatures below 125° F.

Referring now to FIG. 1, the carrier or bandage is made of a flexible, large mesh and preferably knit fabric defining a lattice of relatively large openings 12. The smallest dimension of the openings will generally be at least about 0.015 in$^2$ and preferably is between about 0.02 and 0.05 in$^2$ with a preferred opening size in the vicinity of about 0.026 in$^2$ although opening sizes of as much as 0.25 in$^2$ are feasible. The openings may have any configuration such as square, polygonal or the like. Moreover, the openings are sufficiently large so that in the finished product the polymer composition (hereinafter sometimes referred to as the "coating") does not form air impervious windows across the openings.

The strands 14 of the carrier are preferably formed of relatively coarse, bulky, staple, porous, low density and thermally insulating material such as heavy yarn of 5 to 15 twists having a raw diameter of at least about 0.013 in. and preferably about 0.015 in. to about 0.040 in. When the fluff or fluffs surrounding the yarn strands 14 is included the yarn diameter is, of course, greater; normally it is at least about 0.03 in. and preferably it is in the range of between about 0.050 in. and 0.100 in. although in extreme cases the fluffed diameter may approach 0.200 in.

Materials which may be used for strands 14 include cellulosic materials, such as cotton, synthetic materials such as acrylates and nylon, or combinations thereof. For the most part, organic materials are employed rather than more thermally conductive inorganic materials such as glass fibres. The desired characteristics of the strand material include that it be a thermal insulator, that it provide structural stability to the final product, that it be moldable so that an orthopedic structure, e.g. a cast can be formed therewith, that it is wettable by the coating and that it be stable under normal usage. By way of more specific example, the low density strands of bulky Raschael-type knits formed of staple fibers of cotton and defining naturally occuring multitudinous voids provides a desirable bandage material. A knit of the Raschael-type inherently provides a highly flexible bandage material.

The bandage material further is preferably substantially free of additives which may interfere with the bond between the coating and the fibers. Cellulosic materials are preferably scoured to remove any binders, lubricants or other additives which might inhibit the wetting properties of the polymer or its adhesion to the bandage material.

A preferred bonding or adhesion composition for application to the bandage material is poly-ϵ-caprolactone which is commercially available. Other compositions with similar properties such as the material disclosed in U.S. Pat. No. 3,692,023 can, of course, be substituted. For the purposes of describing the preferred embodiment of this invention, only the poly-ϵ-caprolactone will be referred to and is to be considered illustrative to this family of polymers. For purposes of convenience, the formula set forth in the U.S. patent mentioned in this paragraph is repeated with its definitions as inclusive of the types of polymers which may be employed.

These polymers are characterized by the recurring unit

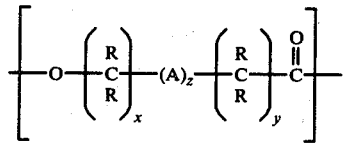

wherein each R, individually is selected from the class consisting of hydrogen, alkyl, halo and alkoxy; A is the oxy group; x is an integer from one to four; y is an integer from one to four; z is an integer of zero to one; with the provisos that (a) the sum of $x + y + z$ is at least four and not greater than seven, and (b) that the total number of R variables which are substituents other than hydrogen does not exceed three, preferably does not exceed three per unit. Illustrative R variables include methyl, ethyl, isopropyl, n-butyl, sec-butyl, t-butyl, hexyl, chloro, bromo, iodo, methoxy, ethoxy, n-butoxy, n-hexoxy, dodecoxy, and the like. It is preferred that each R individually, be hydrogen, lower alkyl, e.g. methyl, ethyl, n-propyl, isobutyl, and/or lower alkoxy, e.g. methoxy, ethoxy, propoxy, n-butoxy, and the like. It is further preferred that the total number of carbon atoms in the R constituents does not exceed 20.

The polymers which are employed will normally have a molecular weight of at least about 30,000 weight average molecular weight and preferably about 40,000 weight average molecular weight will have reduced viscosities as reported in the aforementioned patent of at least above 0.3 and generally not exceeding about 15, commonly above about 0.5 and up to about 10.

Small amounts, generally not exceeding 15 weight percent, more usually not exceeding 10 weight percent, and preferably from about three to eight weight percent of inert insulative fillers may be included in the polymer composition. Such fillers include titanium dioxide, talc, magnesium or calcium carbonate, clay or other suitable inorganic or organic materials.

In the present invention the polymer should thermally soften at or above 125° F., and below about 180° F., and preferably between 145°–165° F.

Referring now to FIG. 5, the method of making bandage roll 2 is briefly described. A supply 16 of bandage or carrier material 4 passes through a first tank 20 beneath a first tank roller 18 for submersion in a coating solution 22.

A variety of solutions may be employed which have varied concentrations of polymer and fillers. A convenient volatile solvent for the polymer is used, for example, a halo carbon such as methylene chloride. A formulation which has been found satisfactory is a mixture of 95 weight percent PCL–700, a poly-ϵ-caprolactone having a weight average molecular weight of about 40,000 (available from the Union Carbide Corporation) and five weight percent of titanium dioxide. The composition is mixed with methylene dichloride to provide a mix having from about five percent to 50 percent solids, preferably from 10 percent to 20 percent the solids content generally being dictated by the required viscosity to render the solution workable. It will be understood that coating techniques may be employed, such as hot melt coatings, where a 100 percent solids content is used.

The initially coated webbing is then passed between adjustable trunnion rolls 24 and past an air knife 26 into an oven 28. A set of guide rolls 30 is disposed in the upper region of the oven and reverses the travel path of the bandage. The air knife blows out any polymer windows in bandage openings 12 (see FIG. 1) which may have formed in passing through the wet polymer solution 22 and it further assists in drying the polymer applied to the wet bandage 4.

As the bandage passes through the oven 28 it is dried at an elevated temperature of around 180° F. If one coat does not provide a sufficiently thick and heavy polymer coating the bandage 4 is subjected to a repeat process by reimmersion in another polymer solution tank and subsequent drying. Corresponding parts of the equipment involved in the repeat process are numbered correspondingly to those parts already described but are suffixed by the letter "a" to distinguish them in the drawings.

Bandage 4 withdrawn from the second oven 28a is wound up into bandage roll 2 with the perforated separator 8 drawn off a separator supply 32.

Referring now to FIGS. 1–4, the thickness of the impregnated strands 14 of bandage 4 was measured in the range of between approximately 0.01 to 0.260 and in the preferred range of between 0.075 and 0.160 in. The size of the openings 12 of the impregnated web were generally somewhat smaller than the previously given sizes of the unimpregnated bandage openings. The smallest size of the coated bandage openings is generally at least 0.010 in$^2$ and preferably it is in the range of between 0.020 in$^2$ to about 0.026 in$^2$, and usually not exceeding 0.050 in$^2$ although coated bandage openings of up to 0.250 in$^2$ appear to be feasible.

Separator 8 is constructed of a material which is inert to both the material of which bandage 4 is constructed and to the polymer composition with which the material is coated. Moreover, the separator material is chosen so that it readily releases from the polymer composition when the composition is in its softened state. Suitable materials for the separator include such materials as low, medium or high density polyethylene, polypropylene, or polystyrene. Moreover, the separator has a multiplicity of relatively small apertures 34 which are evenly distributed over the separator. The separator itself has a width substantially equal to the width of the bandage 4 and, as already mentioned, about the same effective length.

The separator apertures have a size that is smaller than the size of bandage openings 12, normally by a factor of between about 3.5 to about 9 with a presently preferred ratio between the bandage opening size and the separator aperture's size of about 6.5:1. Within the above-mentioned bandage opening sizes the separator apertures therefore have an aperture area in the range of between about 0.003 to about 0.007 in$^2$. For the presently preferred bandage opening area of about 0.026 in$^2$ the presently preferred aperture size is approximately 0.004 in$^2$.

These dimensions translate into separator aperture cross-sectional dimensions "c" of about 0.05 in. to about 0.09 in. with presently preferred cross-sectional dimensions in the range of about 0.06 to 0.07 in.

It is desired that the total "open area" of the separator, that is the combined area of all separator apertures 34 be relatively large. Therefore, the separator is preferably defined by a lattice of crossing strands 36 which are relatively narrow and which have a cross-sectional dimension, or a strand diameter "d" of no more than about 0.01 to about 0.025 in.

With such a dimensioning of the separator, its apertures and its strands a contact between the heat softened polymer composition of adjoining bandage convolutions 6 is minimized and substantially prevented. Furthermore, such a sizing of the separator allows one to employ relatively thin separators which would not normally be considered to effectively separate the heat softened polymer composition of adjoining bandage convolutions. Applicants have found that a separator thickness "t" of between about 0.01 to about 0.05 in. (normally "t" is greater than "d" at points at which perpendicular strands 36 cross) is sufficient to provide the desired separation between adjoining convolutions. This in turn enables one to form a six foot long bandage roll 2 which has an outside diameter normally less than four inches, generally recognized as the maximum feasible diameter which still permits one to hold the roll with one hand during the molding of the orthopedic cast and normally the rolled diameter (for a bandage having the above stated preferred thickness) of no more than about 3.25 in. For comparison, a like bandage roll without a separator has an only slightly lesser diameter (approximately 2.75 in.).

A particularly suitable material for the construction of separator 8 is a plastic netting that is commercially available from the Dupont Corporation under the trademark VEXAR. This is an open mesh material in which a molten polymer is extruded directly into net form in a single operation. VEXAR is available in sheet form in a variety of materials, thicknesses, and with varying aperture sizes and shapes. Four suitable VEXAR separator sheets have the following trade designations and dimensions:

1. VEXAR 10 PDS 169;
    inside aperture dimension: 0.052" × 0.052"
    approximate aperture area: 0.0027 in$^2$
    outside aperture dimension: 0.079" × 0.072"
    strand diameter: 0.01"
    measured separator thickness (overlapped and bonded strands 36): 0.025"
2. 20 PDS 129:
    inside aperture dimension: 0.065" × 0.068"
    approx. aperture size: 0.0044 in$^2$
    outside aperture dimension: 0.110" × 0.100"
    strand diameter: 0.020"
    measured separator thickness: 0.037"
3. 15 ADS 129:
    inside aperture dimension: 0.07" × 0.07"
    approximate aperture area: 0.0049 in$^2$
    outside aperture dimension: 0.1004" × 0.1004"
    strand diameter: 0.014"
    measured separator thickness (overlapped and bonded strands): 0.0265"

Of these tested, commercially available materials, the one carrying the trade designation 15 ADS 129 is presently preferred. It increased the diameter of a six foot long orthopedic bandage roll by only approximately one-fourth inch from 2.75 in. to approximately 3.00 in. Further, as is apparent from the following examples, such a separator reduced the heat up time for a six foot orthopedic bandage roll to approximately the same heat up time required by a bandage roll which had neither a separator nor a "release film". In the following examples, such a bandage roll is identified as the "control sample". In addition, the separator increased the cool down period to roughly twice the cool down period for the control sample.

In the following examples, the heat up and cool down periods for six foot long bandage rolls were determined by immersing the rolls in heated water baths of the indicated temperature and measuring the required time to render the roll sufficiently soft and pliable so that it can be molded into a desired shape, e.g. an orthopedic cast. The cool down period was determined by leaving the roll in tact and measuring the time it took until the roll became sufficiently rigid so that the molding of the bandage became impossible, that is until the bandage became effectively rigid. In all instances, identical bandage materials with identical dimensions and polymer composition coatings were employed.

| SUMMARY OF TIME-TEMPERATURE TESTING HEXCELITE ORTHOPEDIC TAPE | | | |
|---|---|---|---|
| Example 1: Water Temp. | Type Separator | Average (3) Softening Time | Average (4) Hardening Time |
| 150° F | Control (1) | 1.0 min. | 6.0 min. |
|  | Polyethylene (2) | 13.3 min. | 15.0 min. |
|  | Vexar$^R$ | 1.0 min. | 7.2 min. |
| Example 2: |  |  |  |
| 165° F | Control | 0.5 min. | 5.5 min. |
|  | Polyethylene | 8.0 min. | 17.5 min. |
|  | Vexar$^R$ | 0.4 min. | 9.5 min. |
| Example 3: |  |  |  |
| 170° F | Control | 0.3 min. | 3.5 min. |
|  | Polyethylene | 6.8 min. | 19.2 min. |
|  | Vexar$^R$ | 0.3 min. | 9.2 min. |
| Example 4: |  |  |  |
| 175° F | Polyethylene | 5.0 min. | 20.5 min. |
|  | Vexar$^R$ | 0.1 min. | 10.8 min. |
| Example 5: |  |  |  |
| 180° F | Control | 0.1 min. | 5.0 min. |
|  | Polyethylene | 5.5 min. | 21.0 min. |
|  | Vexar$^R$ | 0.1 min. | 10.2 min. |

(1) No separator.
(2) 2 mil polyethylene release film.
(3) When material softens and is between 130° F and 150° F.
(4) Time before roll material begins to harden.

From the foregoing examples the efficacy of the separator 8 of the present invention in reducing heat up times and extending cool down periods to acceptable values is apparent. While heat up times are generally compatible with the heat up times for the control sample, the cool down periods are roughly twice that of the control sample although they are somewhat shorter than the cool down periods for polyethylene release films.

The actual use of a bandage roll constructed in accordance with the present invention should now be apparent. To briefly summarize it, the roll is first immersed in a bath of water heated to the desired temperature, say to between 165° F. to about 180° F. Within less than one minute the polymer composition applied to the bandage softens, the bandage is withdrawn from the bath and it is then formed into an orthopedic cast by unrolling it, for example, about a patient's limb. To prevent loose separator material from interfering with the cast forming operation, the separator may be constructed in separator sections 10 as above described which can be immediately discarded.

We claim:

1. In a bandage assembly for forming a lightweight orthopedic cast, the assembly including a carrier material defining a multitude of openings; a heat softenable polymer composition applied to the carrier; and a separator constructed of a material which is releasable from the composition when the composition is softened by heat, the material, the composition and the separator being rolled up to define said assembly so that the separator separates adjoining convolutions of the material, the improvement to the separator comprising: a length of separator material having a multitude of passageways distributed substantially fully over its surface area so that a fluid medium can circulate through the passageways of the rolled up material to facilitate the heating of the assembly with such fluid medium preparatory to the formation of an orthopedic cast with the material.

2. An assembly according to claim 1 wherein the separator is constructed of polyethylene.

3. An assembly according to claim 1 wherein the separator is constructed of polypropylene.

4. An assembly according to claim 1 wherein the separator is constructed of polystyrene.

5. An assembly according to claim 1 wherein the passageways have cross-sectional dimensions in the range of about 0.05 inch to about 0.09 inch.

6. An assembly according to claim 5 wherein the cross-sectional dimension of the passageways is between about 0.06 to about 0.07 inch.

7. An assembly according to claim 1 wherein the separator has a thickness of between about 0.01 to about 0.05 inch.

8. An assembly according to claim 7 wherein a separator has a thickness of between about 0.02 to about 0.04 inch.

9. An assembly according to claim 1 wherein the separator is defined by a plurality of serially arranged separator sections, each separator section having a length less than the length of the carrier material.

10. An orthopedic bandage assembly wound into a roll comprising in combination an orthopedic bandage defined by a carrier including relatively large sized openings therethrough and a heat softenable composition applied to the carrier so that the composition can be softened preparatory to the formation of an orthopedic cast by submersing the bandage in a heated fluid medium, whereby the medium can penetrate through the openings into the interior of the roll to heat soften the composition; and a separator wound up with the carrier and forming part of the assembly, the separator being constructed of a readily pliable, relatively thin material which readily releases from the composition to prevent the composition of adjacent carrier convolutions in the roll from adhering to each other when the roll is immersed in the heated fluid medium, the separator defining a multiplicity of apertures having a cross-sectional area in the range of between about 0.003 to about 0.007 in.; whereby the separator facilitates said penetration of the roll by the heated fluid medium without significantly increasing the time required to raise the temperature of an inner portion of the roll to the desired level while the carrier significantly prolongs the required time for cooling the composition to below its softening temperature.

11. An assembly according to claim 10 wherein the carrier has a thickness in the range of between about 0.075 and about 0.160 inch and wherein the separator has a thickness of no more than about 0.05 inch.

12. An assembly according to claim 10 wherein the bandage material has a length of at least about six feet and the rolled up assembly has a diameter of no more than about 3.00 inch.

13. An orthopedic bandage assembly for direct application to a body portion requiring an orthopedic cast, the assembly comprising a pliant fabric carrier defined by strands of a relatively bulky material and defining openings having an area of more than 0.010 in$^2$; the strands being coated and at least partially impregnated with a polymer composition having a heat softening point of not less than about 125° F.; and a separator wound up with the polymer composition coated and impregnated fabric carrier into a readily handheld bandage roll, the separator having a thickness so that bandage roll defined by a carrier of approximately six foot length has a diameter not substantially greater than about 3.25 inch, the separator being further constructed of a material which readily releases from the heated composition, the separator further including a multitude of evenly distributed apertures therethrough, the apertures having a size in the range of between about 0.003 in$^2$ to about 0.007 in$^2$; whereby the rolled up assembly can be quickly heat softened by immersing the roll in heated water of a temperature in the range of between about 150° F. to about 180° F. while the thusly heated roll remains in its soft state for between about seven to 10 minutes to permit the formation of the cast before the composition re-hardens.

14. An assembly according to claim 13 wherein the polymer coated strands have a diameter between about 0.10 to 0.260 inch.

15. An assembly according to claim 13 wherein the coated strand have a diameter between about 0.075 inch and 0.160 inch.

16. An assembly according to claim 13 wherein the separator has a thickness of between about 0.01 to about 0.05 inch.

17. An assembly according to claim 15 wherein the separator has a thickness of about 0.02 inch.

18. An assembly according to claim 13 wherein the separator has a width about equal to the width of the carrier material and a length substantially less than the length of the carrier material, and further including a plurality of serially arranged separators placed within the rolled up carrier material and having an effective combined length about equal to the length of the carrier material.

19. An orthopedic bandage assembly usable for forming a lightweight orthopedic cast, the assembly comprising: an elongate, pliable carrier having a length of at least about six feet wound up into a roll having a multitude of adjoining carrier convolutions, the carrier including substantially evenly distributed openings therethrough having an area in the range of between about 0.02 to about 0.05 in$^2$; a heat softenable composition applied to the carrier having a heat softening point of at least about 125° F.; and a separator wound up with the carrier into the roll, the roll including the carrier and the separator having an outer diameter of not substantially more than about four inches, the separator being constructed of a material which is inert relative to the carrier and the composition and which readily releases from the latter so as to prevent the adjoining carrier convolutions of the roll from adhering to each other when the composition is heated to above its softening temperature, the separator having a width substantially equal to the width of the carrier and an effective length substantially equal to the length of the carrier, the separator further including a multiplicity of evenly distributed apertures extending therethrough and having an area less than the area of the carrier openings so that the composition can be heated by immersing the roll in water having a temperature range of between about 150° F. to about 180° F. and such heated water can penetrate the roll at least partially in a radial direction; whereby the rolled by assembly can be heated to above the softening temperature for the composition within no more than about one minute while the composition on the wound up bandage assembly retains its softened state for at least about seven minutes to provide sufficient time to form the cast.

20. A bandage assembly according to claim 19 wherein the ratio between the opening size and the aperture size is in the range of between about 3.7 to about 8.7.

21. A bandage assembly according to claim 20 wherein said ratio is about 6.5.

22. A bandage assembly according to claim 19 wherein the apertures have cross-sectional dimensions in the range of between about 0.05 to about 0.09 inch.

23. A bandage assembly according to claim 22 wherein the cross-sectional dimensions of the apertures are in the range of between about 0.06 to about 0.07 inches.

24. A bandage assembly according to claim 23 wherein the separator is formed by angularly inclined, crossing strands having a strand diameter in the range of between about 0.01 inch to about 0.025 inch.

25. A bandage assembly according to claim 24 wherein the strand diameter is about 0.02.

26. In a method of forming an orthopedic cast by providing a length of a pliable fabric material having openings therethrough which range in size between about 0.01 in$^2$ and about 0.25 in$^2$; attaching a polymer composition to the material which softens at a temperature above about 125° F.; winding the material into a roll; softening the composition by immersing the roll in a heated body of water; and thereafter forming the cast by unwinding the fabric material from the roll and applying it to a body portion, the improvement to the steps of softening the composition and unwinding the material comprising the steps of: physically separating convolutions of the fabric material forming the roll to prevent adjacent fabric convolutions from adhering to each other when the composition is heated; flowing at least a portion of the water during the heating step in a generally radial direction from a periphery of the roll towards the center thereof to thereby shorten the time it takes to fully heat and soften the composition; and prolonging the time during which the composition remains above its heat softening temperature after the roll has been removed from the water over what such time would be if the roll is formed of fabric material and the polymer composition attached thereto only.

27. A method according to claim 26 including the step of placing a separator between adjacent convolutions of the fabric material, the separator being constructed of a material readily releasable from the heat softened composition, and forming a multiplicity of apertures in the separator, and wherein the step of flowing the water in a radial direction is performed by flowing the water through the apertures.

28. A method according to claim 27 wherein the step of prolonging is performed by inhibiting the flow of air through the openings in the rolled up fabric material.

29. A method according to claim 28 wherein the step of inhibiting comprises the steps of forming the apertures so that their cross-section is less than the cross-section of the openings in the fabric material.

30. A method of forming an orthopedic cast comprising the steps of: providing a pliant fabric carrier defined by interwoven strands, the strands forming openings through the carrier having a cross-section in the range of between about 0.10 in$^2$ to about 0.25 in$^2$; applying to the strands a polymer composition which softens when heated to at least about 125° F.; providing a separator constructed of a material which readily releases from the heat softened composition and which includes a multiplicity of evenly distributed apertures of a size substantially smaller than the size of the openings, the separator having a thickness which is significantly less than the thickness of the fabric carrier, the separator further having a width approximately equal to the width of the fabric carrier; rolling a length of at least about six feet of fabric carrier into a roll and placing the separator between adjacent convolutions of the wound up carrier to thereby space apart the convolutions and prevent their adherence to each other when the composition is heat softened; the resulting roll having a diameter which is sufficiently small so that it can be readily held in one hand; heating the composition to above its softening temperature within no more than about one minute by immersing the roll in a body of heated water of a temperature in the range of between about 150° F. to about 180° F. and flowing at least part of the water in a radial direction from an outer surface of the roll past the opening and the apertures towards a center thereof; thereafter removing the roll from the body of water and retaining the temperature of the composition of the roll above the softening temperature for at least about seven minutes; unwinding the fabric carrier from the roll while forming the orthopedic cast; and removing the separator from the roll as the fabric carrier is unwound.

31. A method according to claim 23 wherein the step of removing comprises the steps of severing the separator into a plurality of separator sections, each of which has a length substantially shorter than the length of the fabric carrier, and sequentially removing the sections as the carrier is unwound.

* * * * *

UNITED STATES PATENT AND TRADEMARK OFFICE
CERTIFICATE OF CORRECTION

PATENT NO. : 4,143,655
DATED : March 13, 1979
INVENTOR(S) : Milton F. Custer, Carol J. Laufenberg It is certified that error appears in the above-identified patent and that said Letters Patent are hereby corrected as shown below:

Claim 31, line 1, delete "23" and substitute therefor --30--.

Signed and Sealed this

Third Day of July 1979

[SEAL]

Attest:

Attesting Officer

LUTRELLE F. PARKER
Acting Commissioner of Patents and Trademarks